US008802134B2

(12) United States Patent
Higo et al.

(10) Patent No.: US 8,802,134 B2
(45) Date of Patent: Aug. 12, 2014

(54) PATCH AND METHOD FOR PRODUCING THE SAME

(71) Applicant: Hisamitsu Pharmaceutical Co., Inc., Tosu (JP)

(72) Inventors: Naruhito Higo, Chiyoda-ku (JP); Tetsurou Tateishi, Tsukuba (JP); Takaaki Terahara, Tosu (JP); Kazunosuke Aida, Tsukuba (JP); Shigeki Hayashi, Tosu (JP); Nobuo Tsutsumi, Chiyoda-ku (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 0 days.

(21) Appl. No.: 13/772,843

(22) Filed: Feb. 21, 2013

(65) Prior Publication Data
US 2014/0161865 A1 Jun. 12, 2014

(30) Foreign Application Priority Data
Dec. 6, 2012 (JP) ................................. 2012-267026

(51) Int. Cl.
*A61K 9/00* (2006.01)
*A61F 13/02* (2006.01)

(52) U.S. Cl.
USPC ......................................... 424/448; 424/400

(58) Field of Classification Search
None
See application file for complete search history.

(56) References Cited

U.S. PATENT DOCUMENTS

| | | | | | |
|---|---|---|---|---|---|
| 5,308,621 | A | * | 5/1994 | Taylor et al. | 424/401 |
| 5,906,830 | A | * | 5/1999 | Farinas et al. | 424/448 |
| 2004/0047893 | A1 | | 3/2004 | Dohner et al. | |
| 2004/0057985 | A1 | | 3/2004 | Bracht | |
| 2004/0142024 | A1 | | 7/2004 | Chono et al. | |
| 2005/0260255 | A1 | | 11/2005 | Terahara et al. | |
| 2006/0165763 | A1 | | 7/2006 | Ito et al. | |
| 2008/0038328 | A1 | | 2/2008 | Higo et al. | |
| 2008/0226698 | A1 | | 9/2008 | Tang et al. | |

FOREIGN PATENT DOCUMENTS

| | | | |
|---|---|---|---|
| EP | 0 304 227 | A2 | 2/1989 |
| EP | 1 074 251 | A1 | 2/2001 |
| EP | 1 366 762 | A1 | 12/2003 |
| EP | 1 547 589 | A1 | 6/2005 |
| JP | 63-93714 | A | 4/1988 |
| JP | 2000-505061 | A | 4/2000 |
| JP | 2002-504070 | A | 2/2002 |
| JP | 2004-83519 | A | 3/2004 |
| JP | 2004-83523 | A | 3/2004 |
| JP | 2006-169238 | A | 6/2006 |
| JP | 2010-521525 | A | 6/2010 |
| WO | WO 97/10812 | A2 | 3/1997 |
| WO | WO 01/07018 | A1 | 2/2001 |
| WO | WO 2008/115371 | A2 | 9/2008 |
| WO | WO 2011/136283 | A1 | 11/2011 |
| WO | WO 2012/165253 | A1 | 12/2012 |
| WO | WO 2012/165254 | A1 | 12/2012 |
| WO | WO 2013/081102 | A1 | 6/2013 |

OTHER PUBLICATIONS

Oxybutynin HCI, SciFinder, accessed Jan. 6, 2014, pp. 1-3.*
Japanese Office Action issued Jan. 23, 2013 in Patent Application No. 2012-267026 with English Translation.
"Basic Course in Drug Development XI", Second impression of the first edition, Apr. 20, 1974, pp. 424-427 and additional page (with English translation).
"Pharmaceutical Skin Penetration Enhancement", Drugs and the pharmaceutical sciences, vol. 59, 1993, pp. 243-267 and cover pages.
U.S. Appl. No. 13/923,828, filed Jun. 21, 2013, Aida, et al.
Office Action issued Aug. 19, 2013 in Japanese Patent Application No. 2013-137147 (with partial English-language translation).
Extended European Search Report issued Oct. 9, 2013 in Patent Application No. 13156572.3.
Extended European Search Report issued Aug. 13, 2013 in Patent Application No. 13173633.2.
Anna Rocco, et al., "Analysis of phytosterols in extra-virgin olive oil by nano-liquid chromatography", Journal of Chromatography A, XP002707964A, vol. 1216, No. 43, 2009, pp. 7173-7178.

* cited by examiner

*Primary Examiner* — Scott Long
*Assistant Examiner* — Lyndsey Beckhardt
(74) *Attorney, Agent, or Firm* — Oblon, Spivak, McClelland, Maier & Neustadt, L.L.P.

(57) ABSTRACT

A method for producing a patch having a high skin penetrability and a high pharmaceutical physical properties such as adhesion and cohesiveness, and a long-term storability. The patch is produced by first obtaining an adhesive agent layer composition containing oxybutynin and/or salt thereof as a drug, an acrylic-based polymer and/or a rubber-based polymer as an adhesive base agent, liquid paraffin, an organic acid, and a tackifier; heating the adhesive agent layer composition at a temperature in a range from a melting point of the drug to a temperature higher than the melting point by 10° C. for 2 to 24 hours; and slowly cooling the heated adhesive agent layer composition to obtain the adhesive agent layer comprising the drug at a supersaturated concentration in a dissolved form.

10 Claims, 3 Drawing Sheets

PATCH AND METHOD FOR PRODUCING THE SAME

BACKGROUND OF THE INVENTION

1. Field of the Invention

The present invention relates to a patch and a method for producing the patch. More specifically, the present invention relates to a patch using oxybutynin as a drug and a method for producing the patch.

2. Related Background Art

Conventionally, the oral administration method using a tablet, a capsule, a syrup, or the like has been known as a drug administration method. In recent years, the transdermal administration method has been studied in which a drug is transdermally administered by using a patch. The method using a patch can solve problems associated with the oral administration method, and has advantages such as reduction in frequency of administration, improvement in compliance, and ease of administration and discontinuation. For these reasons, the transdermal administration method is expected as a drug administration method useful especially in a case of elderly or child patients.

The stratum corneum of the normal skin has a barrier function of preventing foreign substances from entering the body. Because of the barrier function, the use of conventional patches often ends up with insufficient transdermal absorption of the formulated drug ingredient. Moreover, since the stratum corneum is highly lipophilic, the skin penetrability of a drug is extremely low, in general.

In a generally known method for enhancing the skin penetrability of a drug in the transdermal administration method, the drug is contained at a supersaturated concentration in a transdermal preparation, and the difference in concentration gradient of the drug is utilized, as described in "Pharmaceutical Skin Penetration Enhancement," edited by K A Walters and J Hadgraft, (the United States), Vol. 59, Marcel Dekker, 1993, pp. 243-267. For example, Japanese Patent Application Publication No. Sho 63-93714 (Patent Literature 1) describes a patch comprising an adhesive agent layer containing a drug at a supersaturated concentration. However, the method in which a drug is contained at a supersaturated concentration in an adhesive agent layer of a patch involves an increased possibility of crystal precipitation of the drug. Hence, the method has problems associated with the crystal precipitation, such as reduction in cohesiveness and adhesion of the adhesive agent layer and reduction in skin penetrability due to a reduced drug release rate. Furthermore, Patent Literature 1 describes melting of crystals of the drug precipitated during storage by heating before use. However, such a method requires the heating operation every time the patch is used, and hence has problems in terms of convenience and ease of administration.

Meanwhile, International Application Japanese-Phase Publication No. 2010-521525 (Patent Literature 2) proposes a transdermal delivery device in which a drug is contained at a supersaturated concentration in an amorphous form in an adhesive matrix. Oxybutynin is listed as an example of the drug. Moreover, as methods for obtaining the drug at a supersaturated concentration in an amorphous form, Patent Literature 2 describes a method in which an adhesive matrix solution containing the drug at a subsaturated concentration is used, or a method in which an adhesive matrix containing the drug at a supersaturated concentration is heated at a temperature exceeding the melting point of the drug. However, when the drug is caused to be present in an amorphous form in the adhesive agent layer in such a manner, the drug is still in a solid form. Hence, the method has the following problems: insufficient pharmaceutical physical properties such as adhesion and cohesiveness; crystal precipitation with the elapse of time; and low release rate of the drug at an initial stage of application of the patch.

On the other hand, Japanese Patent Application Publication No. 2004-83519 (Patent Literature 3) describes a patch using oxybutynin as a drug. The patch is enabled to achieve both skin absorption property of the drug and pharmaceutical physical properties at high levels by introducing, as adhesive base agents, an acrylic-based polymer and a rubber-based polymer at a specific mass ratio into an adhesive agent layer. Patent Literature 3 also states that the drug concentration in the adhesive agent layer may be a supersaturated concentration.

SUMMARY OF THE INVENTION

However, the present inventors have found that, even in the patch as described in Patent Literature 3, crystals of the drug precipitate with the elapse of time in a long-term storage in some cases, and a better long-term storability is required. Particularly in cold districts such as those influenced by the Great East Japan Earthquake, or under harsh conditions where no storage facility is present, the problem of the crystal precipitation tends to come to the surface, and a higher level of long-term storability is required. In this respect, the present inventors have conducted study for further improvement. As a result, the present inventors have found that a trace amount of crystals of a drug may precipitate in an adhesive agent layer during production depending on the production conditions of a patch, and these crystals serve as nucleus to cause the above-described crystal precipitation with the elapse of time. It has also been found that the possibility of crystal precipitation with the elapse of time tends to be high, especially when oxybutynin is used as the drug.

The present invention has been made in view of the problems of the conventional technologies, and an object of the present invention is to provide a method for producing a patch using oxybutynin and/or a pharmaceutically acceptable salt thereof as a drug and a patch obtained by the method. Here, the method is capable of producing a patch which comprises the drug at a supersaturated concentration in a dissolved form in an adhesive agent layer, can be stored for a long period even under harsh conditions where no storage facility is present as in the case of the aftermath of the Great East Japan Earthquake, and can achieve both skin penetrability and pharmaceutical physical properties at high levels.

The present inventors have conducted earnest study to achieve the above object. As a result, the present inventors have found that, in a method for producing a patch using oxybutynin and/or a pharmaceutically acceptable salt thereof as a drug, the drug can be contained in a completely dissolved form even at a supersaturated concentration in an adhesive agent layer by blending a specific adhesive base agent, liquid paraffin, organic acid, and tackifier, heating the blend for a long period at a temperature in a specific range from the melting point of the drug, inclusive, to a temperature higher than the melting point by certain degrees, and then gently cooling the heated blend at a specific rate of temperature drop. In addition, it has been found that the thus obtained patch achieves a high level of skin penetrability, and high levels of pharmaceutical physical properties such as adhesion and cohesiveness. Furthermore, it has been found that such a patch can also achieve a high level of long-term storability, and can be stored for a long period even under harsh conditions where no storage facility is present as in the case of the aftermath of the Great East Japan Earthquake, and that the excellent skin penetrability and the pharmaceutical physical properties as described above are retained because no crystal precipitation occurs for a long period. These findings have led to the completion of the present invention.

Specifically, a method for producing a patch of the present invention is as follows.

[1] A method for producing a patch comprising a support layer and an adhesive agent layer arranged on at least one surface of the support layer, the method comprising:

a step A of obtaining an adhesive agent layer composition comprising at least one selected from the group consisting of oxybutynin and a pharmaceutically acceptable salt thereof as a drug, at least one selected from the group consisting of an acrylic-based polymer and a rubber-based polymer as an adhesive base agent, liquid paraffin, an organic acid, and a tackifier;

a step B of heating the adhesive agent layer composition at a temperature in a range from a melting point (° C.) of the drug to a temperature higher than the melting point by 10° C. for 2 to 24 hours; and a step C of cooling the heated adhesive agent layer composition to a temperature lower than the melting point of the drug at an average rate of temperature drop of 1 to 20° C./hour, thereby obtaining the adhesive agent layer comprising the drug at a supersaturated concentration in a dissolved form.

[2] The method for producing a patch according to [1], wherein a content of the oxybutynin and the pharmaceutically acceptable salt thereof in the adhesive agent layer composition in terms of free oxybutynin is an amount which results in 10 to 50% by mass in the obtained adhesive agent layer.

[3] The method for producing a patch according to [1] or [2], wherein the adhesive agent layer composition comprises, as the adhesive base agent, the acrylic-based polymer and the rubber-based polymer at a mass ratio (a mass of the acrylic-based polymer:a mass of the rubber-based polymer) of 1:4 to 1:19.

[4] The method for producing a patch according to any one of [1] to [3], wherein a mass ratio of the oxybutynin and the pharmaceutically acceptable salt thereof to the liquid paraffin (a mass in terms of free oxybutynin:a mass of liquid paraffin) is 0.5:1 to 1.2:1 in the adhesive agent layer composition.

[5] The method for producing a patch according to any one of [1] to [4], wherein the adhesive agent layer composition comprises the acrylic-based polymer as the adhesive base agent, and the acrylic-based polymer is at least one selected from the group consisting of copolymers of polymethyl methacrylate with a polyacrylate comprising at least one selected from 2-ethylhexyl acrylate, butyl acrylate, diacetone acrylamide, and tetraethylene glycol dimethacrylate, 2-ethylhexyl acrylate-N-vinyl-2-pyrrolidone-1,6-hexane glycol dimethacrylate copolymer, aminoalkyl methacrylate copolymer E, and 2-ethylhexyl acrylate-vinyl acetate copolymer.

[6] The method for producing a patch according to any one of [1] to [5], wherein the adhesive agent layer composition comprises the rubber-based polymer as the adhesive base agent, and the rubber-based polymer is at least one selected from the group consisting of styrene-isoprene-styrene block copolymer, styrene-butadiene-styrene block copolymer, styrene-butadiene rubber, polyisobutylene, isoprene rubber, and silicon rubber.

[7] The method for producing a patch according to any one of [1] to [6], wherein the organic acid is at least one selected from the group consisting of acetic acid, citric acid, and salts thereof.

[8] The method for producing a patch according to any one of [1] to [7], wherein the tackifier is at least one selected from the group consisting of hydrogenated rosin glycerin ester, alicyclic saturated hydrocarbon resins, aliphatic hydrocarbon resins, and terpene resins.

[9] The method for producing a patch according to any one of [1] to [8], further comprising, after the step A and before the step B, a step D1 of applying the adhesive agent layer composition obtained in the step A onto the at least one surface of the support layer.

[10] The method for producing a patch according to any one of [1] to [8], further comprising, after the step B and before the step C, a step D2 of applying the heated adhesive agent layer composition obtained in the step B onto the at least one surface of the support layer.

A patch of the present invention is a patch obtained by the method for producing a patch according to any one of [1] to [10], the patch comprising the support layer and the adhesive agent layer arranged on the at least one surface of the support layer, wherein the adhesive agent layer comprises at least one selected from the group consisting of the oxybutynin and the pharmaceutically acceptable salt thereof as the drug, at least one selected from the group consisting of the acrylic-based polymer and the rubber-based polymer as the adhesive base agent, the liquid paraffin, the organic acid, and the tackifier, and the drug is contained at a supersaturated concentration in a dissolved form.

Note that although it is not exactly clear why the object can be achieved by the present invention, the present inventors speculates as follows. Specifically, in the method for producing a patch of the present invention, first, the adhesive agent layer composition is held for 2 hours or more within a specific temperature range of from the melting point of the contained drug, inclusive, to a temperature higher than the melting point by 10° C., to thereby completely dissolve crystals and crystallization nuclei, even if present. Subsequently, the adhesive agent layer composition is gently cooled at an average rate of temperature drop of 1 to 20° C./hour. Thus, the drug can be contained in a completely dissolved form in the adhesive agent layer, even when the drug concentration is a supersaturated concentration. Furthermore, this state can be retained stably for a long period. In addition, in the method for producing a patch of the present invention, the drug can be contained in a completely dissolved form in the adhesive agent layer also by conducting such a step of dissolving crystals after the crystals are precipitated in the adhesive agent layer composition and on a surface thereof.

Moreover, since the drug is contained at a supersaturated concentration in a dissolved form in the adhesive agent layer as described above, the patch of the present invention achieves both a high level of skin penetrability and high levels of pharmaceutical physical properties. Moreover, since crystal precipitation of the drug is sufficiently suppressed even in a long-term storage, the excellent skin penetrability and pharmaceutical physical properties are retained.

In contrast, the dissolving (melting) conditions of the drug are not controlled sufficiently in conventional methods for producing a patch. The present inventors speculate that, for this reason, it is difficult to make the adhesive agent layer contain stably the drug at a supersaturated concentration in a completely dissolved form, and a trace amount of crystals of the drug remain or precipitate, and serve as nucleus to cause crystal precipitation with the elapse of time. In addition, in the method described in Patent Literature 2 whose object is to obtain the drug in an amorphous form, rapid heating is conducted in a short period at a temperature far higher than the melting point of the drug, and the cooling was conducted without any particular limitation, in contrast to those of the present invention whose object is to obtain the drug in a completely dissolved form.

Note that, in the present invention, the phrase "a drug at a supersaturated concentration" means that the drug is present in the adhesive agent layer in an amount not smaller than the saturated solubility in the adhesive agent layer at room temperature (25° C.). When the drug is a salt, the concentration of the drug refers to a concentration obtained by converting the mass of the salt to the mass of the drug in the free form.

Moreover, in the present invention, dissolution of a drug refers to a state where the drug is scattered in a molecular state in a solvent (the adhesive agent layer, the adhesive agent layer composition, or the like). In addition, whether the drug is in a dissolved form can be checked by the fact that neither an endothermic melting point peak attributable to crystals nor a baseline shift due to a glass transition attributable to an amorphous form is observed in differential scanning calorimetry (DSC). In addition, for example, when the drug is oxybutynin, the endothermic melting point peak (melting point) can be determined from a peak observed in a thermogram obtained by conducting a DSC measurement in which crystals of the drug are heated by using a differential scanning calorimeter from −90° C. to 80° C. at a rate of temperature rise of 10° C./min. Moreover, the glass transition temperature can be determined from a baseline shift observed in a thermogram obtained by conducting a DSC measurement, in which the sample subjected to the measurement for endothermic melting point peak is cooled rapidly to −90° C. to obtain a amorphous form, and then the temperature is again raised from approximately −90° C. to approximately 80° C.

The present invention makes it possible to provide a method for producing a patch using oxybutynin and/or a pharmaceutically acceptable salt thereof as a drug, and a patch obtained by the method. Here, the method is capable of providing a patch which comprises the drug at a supersaturated concentration in a dissolved form in a adhesive agent layer, can be stored for a long period even under harsh conditions where no storage facility is present as in the case of the aftermath of the Great East Japan Earthquake, and can achieve both skin penetrability and pharmaceutical physical properties at high levels.

DETAILED DESCRIPTION OF THE PREFERRED EMBODIMENTS

Figure 1A:
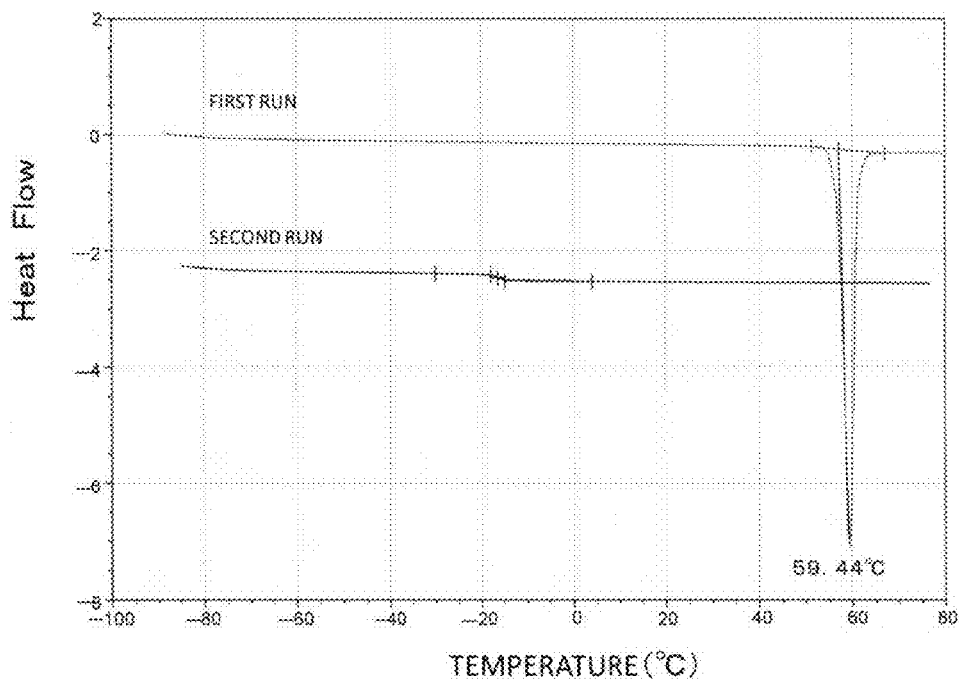
FIG. 1A is a graph showing a result of DSC measurement conducted on crystals of oxybutynin.

Hereinafter, the present invention will be described in detail based on preferred embodiments thereof.

A method for producing a patch of the present invention is a method for producing a patch comprising a support layer and an adhesive agent layer arranged on at least one surface of the support layer, the method comprising:

a step A of obtaining an adhesive agent layer composition comprising at least one selected from the group consisting of oxybutynin and a pharmaceutically acceptable salt thereof as a drug, at least one selected from the group consisting of an acrylic-based polymer and a rubber-based polymer as an adhesive base agent, liquid paraffin, an organic acid, and a tackifier;

a step B of heating the adhesive agent layer composition at a temperature in a range from a melting point (° C.) of the drug to a temperature higher than the melting point by 10° C. for 2 to 24 hours; and a step C of cooling the heated adhesive agent layer composition to a temperature lower than the melting point of the drug at an average rate of temperature drop of 1 to 20° C./hour, thereby obtaining the adhesive agent layer comprising the drug at a supersaturated concentration in a dissolved form.

The method for producing a patch of the present invention is a method for producing a patch comprising a support layer and an adhesive agent layer arranged on at least one surface of the support layer. The support layer according to the present invention is not particularly limited, as long as the support layer is capable of supporting the adhesive agent layer. A stretchable or non-stretchable support layer can be used as the support layer according to the present invention. Especially, one selected from woven fabrics, nonwoven fabrics, and knitted fabrics having water vapor permeability is preferable. The use of a support layer having water vapor permeability makes it possible to effectively release sweat retained between a diseased site and the obtained patch when the patch is applied, and to thereby prevent dampness and skin irritation due to sweat. Specific examples of the support layer include woven fabrics, nonwoven fabrics, and knitted fabrics obtained from synthetic or natural fibers of polyurethane, polyesters, polypropylene, polyvinyl acetate, polyvinylidene chloride, polyethylene, polyethylene terephthalate, aluminum, nylon, acrylic, cotton, rayon, acetate, and the like, or of combinations thereof; composite materials of these fabrics with films having water vapor permeability; and the like. In particular, a knitted fabric made of a polyester is preferable from the viewpoints of safety, versatility, and stretchability.

Moreover, a thickness of the support layer according to the present invention is not particularly limited, and the thickness is preferably in a range from 5 to 1000 μm. If the thickness of the support layer is less than the lower limit value, ease of operation tends to be reduced, when the obtained patch is applied. Meanwhile, if the thickness of the support layer exceeds the upper limit value, ease of production tends to be reduced in the production process of the patch, as exemplified by difficulty in cutting the support layer or the patch.

Moreover, the patch obtained by the production method of the present invention may further comprise a release sheet on a surface of the adhesive agent layer opposite to the surface facing the support layer. Specific examples of the release sheet include films of polyesters such as polyethylene terephthalate, polyvinyl chloride, polyvinylidene chloride, and the like; laminate films of woodfree paper and polyolefin; and the like. These release sheets are preferably subjected to a silicone treatment on a surface to be in contact with the obtained adhesive agent layer, from the viewpoint that ease of operation is increased in peeling the release sheet from the patch.

<Step A>

The method for producing a patch of the present invention comprises a step A of obtaining an adhesive agent layer composition comprising oxybutynin and/or a pharmaceutically acceptable salt thereof as a drug, an acrylic-based polymer and/or a rubber-based polymer as an adhesive base agent, liquid paraffin, an organic acid, and a tackifier.

(Drug)

In the method for producing a patch of the present invention, oxybutynin and/or a pharmaceutically acceptable salt thereof is used as the drug. The pharmaceutically acceptable salt of oxybutynin may be an inorganic salt or an organic salt, and is particularly preferably hydrochloride (i.e., oxybutynin hydrochloride).

By the method for producing a patch of the present invention, the oxybutynin and/or the pharmaceutically acceptable salt thereof is contained at a supersaturated concentration in a dissolved form in the obtained adhesive agent layer. A content of the oxybutynin and the pharmaceutically acceptable salt thereof in the adhesive agent layer composition needs to be a content which results in an amount of supersaturation in the obtained adhesive agent layer in terms of free oxybutynin, from the viewpoint that the obtained patch achieves a high level of skin penetrability of the drug. Specifically, in the present invention, the content of the oxybutynin and the pharmaceutically acceptable salt thereof is preferably an amount which results in 10 to 50% by mass, and more preferably 13 to 20% by mass, although the content cannot be generalized because of dependence on the constitution of the adhesive agent layer. If the content of the oxybutynin and/or the pharmaceutically acceptable salt thereof is less than the lower limit value, the skin penetrability of the drug of the obtained patch tends to decrease. Meanwhile, if the content exceeds the upper limit value, the oxybutynin and/or the pharmaceutically acceptable salt thereof may be incompletely dissolved in the adhesive agent layer, and precipitated by crystallization, and physical properties such as adhesion and/or skin penetrability of the drug tend to deteriorate.

Note that the content in the obtained adhesive agent layer in the present invention refers to a content relative to the entire mass of all the compounds actually contained in the adhesive agent layer obtained by the method for producing a patch of the present invention, and the entire mass of all the compounds actually contained in the adhesive agent layer is equivalent to a mass of non-volatile components in the adhesive agent layer composition, i.e., a mass obtained by subtracting a mass of volatile solvents from the total mass of the adhesive agent layer composition.

In addition, in the method for producing a patch of the present invention, drugs other than oxybutynin may be further incorporated in the adhesive agent layer composition, unless the effects of the present invention are impaired. Such drugs are not particularly limited, and examples thereof include hypnotic and sedative agents (flurazepam hydrochloride, rilmazafone hydrochloride, phenobarbital, amobarbital, and the like), antipyretic and antiinflammatory agents (butorphanol tartrate, perisoxal citrate, acetaminophen, mefenamic acid, diclofenac sodium, aspirin, alclofenac, ketoprofen, flurbiprofen, naproxen, piroxicam, pentazocine, indomethacin, glycol salicylate, aminopyrine, loxoprofen, and the like), steroidal anti-inflammatory agents (hydrocortisone, prednisolone, dexamethasone, betamethasone, and the like), excitants and stimulants (methamphetamine hydrochloride, methylphenidate hydrochloride, and the like), neuropsychiatric drugs (imipramine hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptiline, trazodone, lofepramine, milnacipran, duloxetine, venlafaxine, chlorpromazine hydrochloride, thioridazine, diazepam, meprobamate, etizolam, risperidone, mirtazapine, and the like), hormone drugs (estradiol, estriol, progesterone, norethisterone acetate, metenolone acetate, testosterone, and the like), local anesthetics (lidocaine hydrochloride, procaine hydrochloride, tetracaine hydrochloride, dibucaine hydrochloride, propitocaine hydrochloride, and the like), agents for urinary organs (tamsulosin hydrochloride, propiverine hydrochloride, tolterodine tartrate, fesoterodine, imidafenacin, and the like), skeletal muscle relaxants (tizanidine hydrochloride, eperisone hydrochloride, pridinol mesylate, suxamethonium chloride, and the like), agents for reproductive organs (ritodrine hydrochloride, meluadrine tartrate, and the like), antiepileptic agents (sodium valproate, clonazepam, carbamazepine, and the like), agents for autonomic nerves (carpronium chloride, neostigmine bromide, bethanechol chloride, and the like), antiparkinsonian agents (pergolide mesylate, bromocriptine mesylate, trihexyphenidyl hydrochloride, amantadine hydrochloride, ropinirole hydrochloride, talipexole hydrochloride, cabergoline, droxidopa, biperiden, selegiline hydrochloride, and the like), diuretic agents (hydroflumethiazide, furosemide, and the like), respiratory stimulants (lobeline hydrochloride, dimorpholamine, naloxone hydrochloride, and the like), antimigraine agents (dihydroergotamine mesylate, sumatriptan, ergotamine tartrate, flunarizine hydrochloride, cyproheptadine hydrochloride, and the like), antihistamines (clemastine fumarate, diphenhydramine tannate, chlorpheniramine maleate, diphenylpyraline hydrochloride, promethazine, and the like), bronchodilators (tulobuterol hydrochloride, procaterol hydrochloride, salbutamol sulfate, clenbuterol hydrochloride, fenoterol hydrobromide, terbutaline sulfate, isoprenaline sulfate, formoterol fumarate, and the like), cardiotonics (isoprenaline hydrochloride, dopamine hydrochloride, and the like), coronary vasodilators (diltiazem hydrochloride, verapamil hydrochloride, isosorbide dinitrate, nitroglycerin, nicorandil, and the like), peripheral vasodilators (nicametate citrate, tolazoline hydrochloride, and the like), smoking cessation aids (nicotine and the like), agents for circulatory organs (flunarizine hydrochloride, nicardipine hydrochloride, nitrendipine, nisoldipine, felodipine, amlodipine besilate, nifedipine, nilvadipine, manidipine hydrochloride, benidipine hydrochloride, enalapril maleate, temocapril hydrochloride, alacepril, imidapril hydrochloride, cilazapril, lisinopril, captopril, trandolapril, perindopril erbumine, atenolol, pindolol, bisoprolol fumarate, metoprolol tartrate, betaxolol hydrochloride, timolol maleate, bopindolol malonate, nipradilol, arotinolol hydrochloride, celiprolol hydrochloride, carvedilol, amosulalol hydrochloride, carteolol hydrochloride, bevantolol hydrochloride, terazosin hydrochloride, bunazosin hydrochloride, prazosin hydrochloride, doxazosin mesylate, valsartan, candesartan cilexetil, losartan potassium, clonidine hydrochloride, guanfacine hydrochloride, guanabenz acetate, and the like), antiarrhythmic agents (propranolol hydrochloride, alprenolol hydrochloride, procainamide hydrochloride, mexiletine hydrochloride, nadolol, disopyramide, and the like), anti-malignant-ulcer agents (cyclophosphamide, fluorouracil, tegafur, procarbazine hydrochloride, ranimustine, irinotecan hydrochloride, fluridine, and the like), antilipemic agents (pravastatin, simvastatin, bezafibrate, probucol, and the like), hypoglycemic agents (glibenclamide, chlorpropamide, tolbutamide, glymidine sodium, glybuzole, buformin hydrochloride, and the like), anti-peptic ulcer agents (proglumide, cetraxate hydrochloride, spizofurone, cimetidine, glycopyrronium bromide, and the like), cholagogues (ursodesoxycholic acid, osalmid, and the like), gastroprokinetic agents (domperidone, cisapride, and the like), hepatic disease agents (tiopronin and the like), anti-allergic agents (ketotifen fumarate, azelastine hydrochloride, and the like), antiviral agents (acyclovir and the like), antivertigo agents (betahistine mesylate, difenidol hydrochloride, and the like), antibiotics (cephaloridine, cefdinir, cefpodoxime proxetil, cefaclor, clarithromycin, erythromycin, methylerythromycin, kanamycin sulfate, cycloserine, tetracycline, benzylpenicillin potassium, propicillin potassium, cloxacillin sodium, ampicillin sodium, bacampicillin hydrochloride, carbenicillin sodium, chloramphenicol, and the like), agents for habitual intoxication (cyanamide and the like), appetite suppressants (mazindol and the like), chemotherapeutic agents (isoniazid, ethionamide, pyrazinamide, and the like), blood coagulation accelerators (ticlopidine hydrochloride, warfarin potassium, and the like), anti-Alzheimer's agents (physostigmine, donepezil hydrochloride, tacrine, arecoline, xanomeline, and the like), serotonin receptor antagonist antiemetics (ondansetron hydrochloride, granisetron hydrochloride, ramosetron hydrochloride, azasetron hydrochloride, palonosetron, and the like), antigout agents (colchicine, probenecid, sulfinpyrazone, and the like), narcotic analgesics (fentanyl citrate, morphine sulfate, morphine hydrochloride, codeine phosphate, cocaine hydrochloride, pethidine hydrochloride, and the like), and the like. When such a drug other than oxybutynin is further incorporated, the amount of the drug incorporated is preferably an amount which results in a content of 20% by mass or less in the obtained adhesive agent layer, from the viewpoint that the obtained adhesive agent layer has better cohesiveness and better releasability of oxybutynin, although the preferable amount cannot be generalized because the amount varies depending on the purpose of the treatment.

(Adhesive Base Agent)

In the method for producing a patch of the present invention, an acrylic-based polymer and/or a rubber-based polymer is used as the adhesive base agent. The acrylic-based polymer is an acrylic-based polymer having substantially no carboxyl groups (carboxylic acid groups, —COOH) and substantially no hydroxyl groups (—OH) in a molecule thereof, and is preferably an acrylic-based polymer having, in a molecule thereof, no carboxyl groups and no hydroxyl groups which may serve as reaction sites of cross linking.

Such an acrylic-based polymer can be obtained, for example, by polymerization of a monomer having no carboxyl groups and no hydroxyl groups. Examples of such a monomer include methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, other (meth)acrylic acid esters corresponding to desired acrylic-based polymers, and the like.

The acrylic-based polymer according to the present invention preferably has a viscosity average molecular weight of 200,000 to 1,000,000. If the viscosity average molecular weight of the acrylic-based polymer is less than the lower limit value, pharmaceutical physical properties (especially cohesiveness) of the obtained patch tend to deteriorate. Meanwhile, if the viscosity average molecular weight exceeds the upper limit value, the compatibility of the acrylic-based polymer with other components contained in the adhesive agent layer composition tends to be lowered.

Preferred examples of the acrylic-based polymer according to the present invention include (a1) block copolymers of polymethyl methacrylate with a polyacrylate comprising at least one selected from 2-ethylhexyl acrylate, butyl acrylate, diacetone acrylamide, and tetraethylene glycol dimethacrylate, (a2) 2-ethylhexyl acrylate-N-vinyl-2-pyrrolidone-1,6-hexane glycol dimethacrylate copolymer, (a3) aminoalkyl methacrylate copolymer E, and (a4) 2-ethylhexyl acrylate-vinyl acetate copolymer.

In addition, as the acrylic-based polymer according to the present invention, commercially available ones can be used as appropriate. For example, DURO-TAK87-2097 (having no functional groups), DURO-TAK87-4098 (having no functional groups) supplied from Henkel AG & Co. KGaA, and the like can be used. Of these acrylic-based polymers, it is more preferable to use 2-ethylhexyl acrylate-N-vinyl-2-pyrrolidone-1,6-hexane glycol dimethacrylate copolymer and/or 2-ethylhexyl acrylate-vinyl acetate copolymer, because both the skin penetrability of the drug and the pharmaceutical physical properties of the obtained patch tend to be enhanced. One of these acrylic-based polymers may be used alone, or two or more thereof may be used in combination.

The rubber-based polymer refers to a natural or synthetic elastic polymer. Preferred examples of such a rubber-based polymer include (b1) styrene-isoprene-styrene block copolymer, (b2) styrene-butadiene-styrene block copolymer, (b3) styrene-butadiene rubber, (b4) polyisobutylene, (b5) isoprene rubber, and (b6) silicon rubber.

Of these rubber-based polymers, it is more preferable to use styrene-isoprene-styrene block copolymer and/or polyisobutylene, because both the skin penetrability of the drug and the pharmaceutical physical properties of the obtained patch tend to be enhanced. One of these rubber-based polymers may be used alone, or two or more thereof may be used in combination.

The rubber-based polymer according to the present invention has a viscosity average molecular weight of preferably 30,000 to 2,500,000, and more preferably 100,000 to 1,700,000. If the viscosity average molecular weight of the rubber-based polymer is less than the lower limit value, pharmaceutical physical properties (especially cohesiveness) of the obtained patch tend to deteriorate. Meanwhile, if the viscosity average molecular weight exceeds the upper limit value, the patch tends to be difficult to produce, because the compatibility of the rubber-based polymer with other components contained in the adhesive agent layer composition is lowered.

Moreover, it is preferable to use at least one selected from 2-ethylhexyl acrylate-N-vinyl-2-pyrrolidone-1,6-hexane glycol dimethacrylate copolymer and 2-ethylhexyl acrylate-vinyl acetate copolymer as the acrylic-based polymer, and styrene-isoprene-styrene block copolymer as the rubber-based polymer, because both the skin penetrability of the drug and the pharmaceutical physical properties of the obtained patch are further enhanced.

In the method for producing a patch of the present invention, the adhesive agent layer composition preferably comprises the acrylic-based polymer and the rubber-based polymer as the adhesive base agent at a mass ratio (a mass of the acrylic-based polymer:a mass of the rubber-based polymer) of 1:4 to 1:19, and more preferably 1: 5 to 1:10. When the mass ratio of the contents is within the range in a case where the oxybutynin and/or the pharmaceutically acceptable salt thereof is used as the drug, the skin penetrability of the drug tends to be further enhanced, and higher levels of pharmaceutical physical properties tend to be achieved. Moreover, when the mass ratio of the contents is within the range, a moderate adhesive force is provided by the obtained adhesive agent layer, and application property and skin irritation tend to be more improved. On the other hand, if the content of the rubber-based polymer relative to the acrylic-based polymer in the adhesive agent layer composition is less than the lower limit, the skin penetrability of the drug of the obtained patch tends to deteriorate. If the content of the rubber-based polymer relative to the acrylic-based polymer exceeds the upper limit, pharmaceutical physical properties of the obtained patch tend to deteriorate.

Regarding a content of the acrylic-based polymer according to the present invention in the adhesive agent layer composition, the mass ratio of the content of the acrylic-based polymer to the content of the rubber-based polymer is preferably in the above-described range. The content of the acrylic-based polymer is not particularly limited, and is preferably an amount which results in a content of 0.5 to 10% by mass, and more preferably 1 to 5% by mass, in the obtained adhesive agent layer. If the content of the acrylic-based polymer is less than the lower limit value, the skin penetrability of the drug of the obtained patch tends to deteriorate. Meanwhile, if the content of the acrylic-based polymer exceeds the upper limit value, the cohesive force of the adhesive agent layer tends to be lowered.

In addition, regarding the content of the rubber-based polymer according to the present invention in the adhesive agent layer composition, the mass ratio of the content of the rubber-based polymer relative to the content of the acrylic-based polymer is preferably within the above-described range. The content of the rubber-based polymer is not particularly limited, and is preferably an amount which results in a content of 5 to 40% by mass, and more preferably 10 to 25% by mass, in the obtained adhesive agent layer. If the content of the rubber-based polymer is less than the lower limit value, the skin penetrability of the drug of the obtained patch tends to deteriorate. Meanwhile, if the content of the rubber-based polymer exceeds the upper limit value, the adhesive force of the adhesive agent layer tends to be lowered.

In addition, in the method for producing a patch of the present invention, an adhesive base agent other than the acrylic-based polymer and the rubber-based polymer may further be incorporated into the adhesive agent layer composition, unless the effects of the present invention are impaired. Examples of such an adhesive base agent other than the acrylic-based polymer and the rubber-based polymer include ethylene-vinyl acetate copolymer (EVA, vinyl acetate content: 5 to 60% by mass), silicone-based polymers such as organopolysiloxanes (silicones), and the like. When these adhesive base agents are further incorporated, the amount of the adhesive base agents incorporated is preferably an amount which results in a content of 10% by mass or less in the obtained adhesive agent layer.

(Liquid Paraffin)

In the step A according to the present invention, liquid paraffin is introduced into the adhesive agent layer composition. The present inventors speculate that, in the present invention, the liquid paraffin functions as a dissolving agent and plasticizer for other compounds (the drug and other incorporated components) in the adhesive agent layer composition, and hence the drug in the obtained patch can be retained for a long period in a state of a supersaturated concentration and a dissolved form.

The liquid paraffin is contained in the adhesive agent layer composition, preferably such that the mass ratio of the mass of the oxybutynin and/or the pharmaceutically acceptable salt thereof in terms of free oxybutynin to the mass of the liquid paraffin (a mass in terms of free oxybutynin:a mass of the liquid paraffin) can be 0.5:1 to 1.2:1, and more preferably 0.7:1 to 1.2:1. If the content of the liquid paraffin is less than the lower limit value, the possibility of crystal precipitation of the drug during long-term storage tends to increase. Meanwhile, if the content exceeds the upper limit value, the obtained adhesive agent layer is excessively softened, so that a phenomenon (remaining of the adhesive agent layer) tends to occur in which the adhesive agent layer remains attached to the skin after detachment of the patch.

(Organic Acid)

In the step A according to the present invention, the organic acid is introduced in the adhesive agent layer composition. An organic acid is generally known to function as a skin penetration enhancer. The present inventors speculate that, in the present invention, the organic acid also functions as a solubilizer for other compounds (the drug and other incorporated components) in the adhesive agent layer composition, and hence the drug in the obtained patch can be retained for a long period in a state of a supersaturated concentration and a dissolved form.

Examples of the organic acid according to the present invention include aliphatic (mono-, di-, or tri-) carboxylic acids (acetic acid (including glacial acetic acid), propionic acid, citric acid (including anhydrous citric acid), isobutyric acid, caproic acid, caprylic acid, lactic acid, maleic acid, pyruvic acid, oxalic acid, succinic acid, tartaric acid, and the like); aromatic carboxylic acids (phthalic acid, salicylic acid, benzoic acid, acetylsalicylic acid, and the like); alkyl sulfonic acids (methanesulfonic acid, ethanesulfonic acid, propanesulfonic acid, butanesulfonic acid, polyoxyethylene alkyl ether sulfonic acids, and the like); alkyl sulfonic acid derivatives (N-2-hydroxyethylpiperidine-N'-2-ethanesulfonic acid; cholic acid derivatives (dehydrocholic acid, and the like); salts thereof (for example, alkali metal salts such as sodium salts); and the like. Of these organic acids, carboxylic acids and salts thereof are preferable, and acetic acid, sodium acetate, citric acid, and salts thereof are particularly preferable. One of these organic acids may be used alone, or two or more thereof may be used in combination.

A content of the organic acid in the adhesive agent layer composition according to the present invention is preferably an amount which results in a content of 0.01 to 20% by mass, more preferably 0.1 to 15% by mass, and further preferably 0.1 to 12% by mass, in the obtained adhesive agent layer. If the content of the organic acid is less than the lower limit value, the possibility of crystal precipitation of the drug during long-term storage tends to increase, or the effect of improving the skin penetrability of the drug by the organic acid tends to be insufficient. Meanwhile, if the content exceeds the upper limit value, the skin irritation of the obtained patch tends to increase.

(Tackifier)

In the step A according to the present invention, a tackifier is introduced into the adhesive agent layer composition. Specific examples of the tackifier according to the present invention include rosin derivatives (rosin, rosin glycerin ester, hydrogenated rosin, hydrogenated rosin glycerin ester, rosin pentaerythritol ester, and the like), alicyclic saturated hydrocarbon resins (ARKON P100 (manufactured by Arakawa Chemical Industries, Ltd.), and the like), aliphatic hydrocarbon resins (Quintone B-170 (manufactured by Zeon Corporation), and the like), terpene resins (Clearon P-125 (manufactured by YASUHARA CHEMICAL CO., LTD), and the like), maleic acid resin, and the like. Of these tackifiers, hydrogenated rosin glycerin ester, alicyclic saturated hydrocarbon resins, aliphatic hydrocarbon resins, and terpene resins are preferable, and alicyclic saturated hydrocarbon resins are particularly preferable.

A content of the tackifier in the adhesive agent layer composition according to the present invention is preferably an amount which results in a content of 10 to 60% by mass, and more preferably 30 to 50% by mass, in the obtained adhesive agent layer. If the content of the tackifier is less than the lower limit value, the effect of improving the adhesive force of the patch by the incorporated tackifier tends to be insufficient. Meanwhile, if the content of the tackifier exceeds the upper limit value, skin irritation during peeling-off of the obtained patch tends to increase.

In addition, when an alicyclic saturated hydrocarbon resin is used as the tackifier, a mass ratio of a total mass of the acrylic-based polymer and the rubber-based polymer to a mass of the alicyclic saturated hydrocarbon resin in the adhesive agent layer composition is preferably 1:1 to 1:3. When the contents of the acrylic-based polymer, the rubber-based polymer, and the alicyclic saturated hydrocarbon resins satisfy the above condition, both the skin penetrability of the oxybutynin and/or the pharmaceutically acceptable salt thereof and pharmaceutical physical properties are further enhanced, and moreover the adhesive force is further enhanced, so that a patch with further improved pharmaceutical physical properties and skin irritation can be obtained.

(Solvent)

In the step A according to the present invention, a solvent may be further incorporated into the adhesive agent layer composition. Especially in a case where the adhesive agent layer composition is applied onto the support layer or the release sheet before the step B described later (in a case of a first method described later), the adhesive agent layer composition preferably further comprises an appropriate amount of a solvent, from the viewpoint that the contained compounds are sufficiently dissolved to obtain a homogeneous composition before the application. Examples of such a solvent include toluene, hexane, ethyl acetate, and the like. One of these solvents may be used alone, or two or more thereof may be used in combination.

(Absorption Enhancer)

Moreover, in the step A according to the present invention, an absorption enhancer may further be incorporated into the adhesive agent layer composition. Conventional compounds known to have an effect of enhancing skin absorption can be used as the absorption enhancer. Specific examples of the absorption enhancer include fatty acids having 6 to 20 carbon atoms, fatty alcohols, fatty acid esters, amides, ethers, aromatic organic acids other than the above-described organic acid, aromatic alcohols, aromatic organic acid esters, ethers, and the like. These compounds may be saturated or unsaturated, and may be linear, branched, or cyclic. Moreover, in the present invention, it is possible to use, as the absorption enhancer, lactic acid esters, acetic acid esters, monoterpene-based compounds, sesquiterpene-based compounds, Azone, Azone derivatives, glycerin fatty acid esters, propylene glycol fatty acid esters, sorbitan fatty acid esters (Span series), polysorbate-based compounds (Tween series), polyethylene glycol fatty acid esters, polyoxyethylene hardened castor oil-based compounds (HCO series), polyoxyethylene alkyl ethers, sucrose fatty acid esters, vegetable oils, and the like. Of these absorption enhancers, preferred are caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanolamide, isopropylmyristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, l-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane, and olive oil, and more preferred are lauryl alcohol, myristyl alcohol, isostearyl alcohol, lauric acid diethanolamide, glycerin monocaprylate, glycerin monocaprate, glycerin monooleate, sorbitan monolaurate, propylene glycol monolaurate, polyoxyethylene lauryl ether, and pirotiodecane. One of these absorption enhancers may be used alone or, two or more thereof may be used in combination.

When such an absorption enhancer is further incorporated, the amount of the absorption enhancer incorporated is not particularly limited, and is preferably an amount which results in a content of 0.01 to 20% by mass, more preferably 0.05 to 10% by mass, and further preferably 0.1 to 5% by mass, in the obtained adhesive agent layer. If the content of the absorption enhancer is less than the lower limit value, the effect of improving the skin penetrability of the drug by the absorption enhancer tends to be insufficient. Meanwhile, if the content of the absorption enhancer exceeds the upper limit value, skin irritation, which causes edema or the like, of the obtained patch tends to increase.

(Plasticizer)

Moreover, in the step A according to the present invention, a plasticizer may further be incorporated into the adhesive agent layer composition. Specific examples of such a plasticizer include petroleum-based oils excluding the liquid paraffin (naphthene-based process oil, aromatic-based process oil, and the like), squalane, squalene, vegetable-based oils (olive oil, camellia oil, castor oil, tall oil, peanut oil), silicon oils, liquid rubbers (polybutene and liquid isoprene rubber), liquid fatty acid esters (isopropyl myristate, hexyl laurate, diethyl sebacate, diisopropyl sebacate, and the like), diethylene glycol, polyethylene glycol, propylene glycol, dipropylene glycol, triacetin, triethyl citrate, crotamiton, cholesterol, and the like. Of these plasticizers, liquid polybutene, crotamiton, diethyl sebacate, hexyl laurate, and cholesterol are particularly preferable. One of these plasticizers may be used alone, or two or more thereof may be used in combination.

When such a plasticizer is further incorporated, the amount of the plasticizer incorporated is not particularly limited, and is preferably an amount which results in a content of 5 to 69.5% by mass, more preferably 10 to 60% by mass, and further preferably 10 to 50% by mass, in the obtained adhesive agent layer. If the content of the plasticizer is less than the lower limit value, the effect of improving the cohesive force of the patch by incorporating the plasticizer tends to be insufficient. Meanwhile, if the content of the plasticizer exceeds the upper limit value, the skin penetrability of the drug of the obtained patch tends to be insufficient.

(Additives)

Moreover, in the step A according to the present invention, additives such as an antioxidant, a filler, and an ultraviolet absorber may further be incorporated into the adhesive agent layer composition, if necessary. Such an antioxidant is preferably tocopherol, an ester derivative thereof, ascorbic acid, ascorbyl stearate, nordihydroguaiaretic acid, dibutylhydroxytoluene (BHT), or butylhydroxyanisole.

In addition, the filler is preferably calcium carbonate, magnesium carbonate, a silicate (for example, aluminum silicate, magnesium silicate, or the like), silicic acid, barium sulfate, calcium sulfate, calcium zincate, zinc oxide, or titanium oxide. Moreover, the ultraviolet absorber is preferably a p-aminobenzoic acid derivative, an anthranilic acid derivative, a salicylic acid derivative, a coumarin derivative, an amino acid-based compound, an imidazoline derivative, a pyrimidine derivative, or a dioxane derivative.

When such additives are further incorporated, amounts of the additives incorporated are not particularly limited, and are preferably amounts which result in a total content of these additives of 10% by mass or less, more preferably 5% by mass or less, further preferably 2% by mass or less, in the obtained adhesive agent layer.

In the step A according to the present invention, the method for obtaining the adhesive agent layer composition is not particularly limited, and the adhesive agent layer composition according to the present invention can be obtained, for example, by mixing together the oxybutynin and/or the pharmaceutically acceptable salt thereof, the acrylic-based polymer and/or the rubber-based polymer, the liquid paraffin, the organic acid, the tackifier, and, if necessary, the solvent and the like. The mixing method is not particularly limited, and the mixing can be conducted by, for example, a method using a mixer, a mortar, or the like.

The mixing is conducted preferably until the adhesive agent layer composition becomes homogeneous. Especially in a case where the adhesive agent layer composition is applied onto the support layer or the release sheet following to the step A according to the present invention and prior to the step B described later (in the case of the first method described later), the mixing is conducted preferably until the compounds contained in the adhesive agent layer composition are sufficiently dissolved, from the viewpoint that a more homogeneous adhesive agent layer composition is applied onto the support layer.

<Step B>

The method for producing a patch of the present invention comprises a step B of heating the adhesive agent layer composition at a temperature in a range from a melting point (° C.) of the drug to a temperature higher than the melting point by 10° C. for 2 to 24 hours. Such a step B may be conducted before or after the step of applying the adhesive agent layer composition. In addition, such a step B may be conducted under a condition where neither crystals nor crystallization nuclei are present in the adhesive agent layer composition. If crystals or crystallization nuclei remain and/or precipitate with the elapse of time in the adhesive agent layer composition, the step B may be conducted after such precipitation. Hereinafter, the method further comprising, after the step A and before the step B, a step D1 of applying the adhesive agent layer composition obtained in the step A onto the at least one surface of the support layer (order of steps: A, D1, B, and C) is referred to as a first method, whereas the method further comprising, after the step B and before the step C, a step D2 of applying the heated adhesive agent layer composition obtained in the step B onto the at least one surface of the support layer (order of steps: A, B, D2, and C) is referred to as a second method.

(First Method)

In the first method, the adhesive agent layer composition obtained in the step A is applied onto the at least one surface of the support layer in the step D1, and then heated at a temperature in a range from a melting point (° C.) of the drug to a temperature higher than the melting point by 10° C. for 2 to 24 hours in the step B.

Since the adhesive agent layer composition is first applied onto the support layer in the first method, the compounds contained in the adhesive agent layer composition are preferably sufficiently dissolved in the step A. For such a sufficient dissolution, the adhesive agent layer composition preferably comprises the solvent and the like. In the step D1, the adhesive agent layer composition may be applied onto both surfaces of the support layer. However, the adhesive agent layer composition is preferably applied onto any one of the surfaces of the support layer, from the viewpoint that the production can be achieved by a simpler process.

In addition, when the patch obtained by the production method of the present invention further comprises the release sheet, the adhesive agent layer composition obtained in the step A may be applied onto a surface of the release sheet instead of the support layer in the step D1, and then heated in the step B.

In the step D1, the application method is not particularly limited, and a method used in a conventional method for producing a patch can be employed as appropriate. Moreover, a thickness of the application is not particularly limited, and is preferably a thickness which results in a thickness of the obtained adhesive agent layer of about 20 to about 200 μm. When the thickness of the obtained adhesive agent layer is less than the lower limit value, the skin penetrability of the drug of the obtained patch tends to be insufficient. Meanwhile, if the thickness of the obtained adhesive agent layer exceeds the upper limit value, a phenomenon (remaining of the adhesive agent layer) tends to occur in which the adhesive agent layer remains attached to the skin after the detachment of the obtained patch.

The first method preferably further comprises a drying step of drying the applied adhesive agent layer composition following to the step D1. Regarding conditions of such drying, the drying is preferably conducted under conditions of a temperature lower than the melting point of the drug and shorter than 2 hours.

In addition, the first method may further comprise, before the step B:

a laminating step of laminating the release sheet or the support layer on a surface of the applied or dried adhesive agent layer composition, the surface being opposite to the surface facing the support layer or the release sheet;

a cutting step of cutting a laminate comprising the support layer and/or the release sheet and the applied (preferably dried) adhesive agent layer composition into pieces with desired sizes; and a packaging step of packaging the pieces of the laminate into packaging containers. Note that specific examples of the packaging containers include pouch-shaped containers and molded containers made of metal foils such as aluminum foil; films with low oxygen permeability such as ethylene-vinyl alcohol copolymer films, metal (aluminum or the like) deposited plastic films, and ceramic (silicon oxide or the like) deposited plastic films; metals such as stainless steel; glass; laminated films of any of these with a polyacrylonitrile film, a polyethylene film, a cellulose film, or the like.

A heating temperature in the step B according to the present invention needs to be in a range from a melting point (° C.) of the drug to a temperature higher than the melting point by 10° C. If the heating temperature is lower than the lower limit value, crystals of the drug remain or precipitate in the obtained adhesive agent layer, so that the drug cannot be contained at a supersaturated concentration in a dissolved form. Meanwhile, if the heating temperature exceeds the upper limit value, the drug tends to be in an amorphous form in the subsequent cooling step, which makes it difficult for the drug to be contained in a dissolved form in the adhesive agent layer. Moreover, pharmaceutical physical properties such as adhesion and cohesiveness of the obtained patch deteriorate. In addition, the heating temperature is preferably in a range from the melting point (° C.) of the drug to a temperature higher than the melting point by 5° C., from the viewpoints that the drug can be more efficiently contained at a supersaturated concentration in a dissolved form in the adhesive agent layer, that crystal precipitation of the drug can be suppressed for a longer period, and further that better pharmaceutical physical properties tend to be achieved.

In addition, a heating time in the step B according to the present invention needs to be in a range from 2 to 24 hours. If the heating time is shorter than the lower limit value, crystals of the drug precipitate with the elapse of time in the obtained adhesive agent layer. Meanwhile, if the heating time exceeds the upper limit value, further increase in the effect of suppressing the crystal precipitation of the drug cannot be expected by employing such a long heating time, and such a heating time is economically disadvantageous. In addition, the heating time is preferably 2 to 20 hours, and more preferably 6 to 20 hours, from the viewpoint that there are tendencies that the drug can be more efficiently contained at a supersaturated concentration in a dissolved form in the adhesive agent layer, and that crystal precipitation of the drug can be suppressed for a longer period.

(Second Method)

In the second method, first, the adhesive agent layer composition obtained in the step A is heated at a temperature in a range from the melting point (° C.) of the drug to a temperature higher than the melting point by 10° C. for 2 to 24 hours in the step B, and then the heated adhesive agent layer composition is applied onto the at least one surface of the support layer in the step D2.

In the second method, the step D2 is the same as the step D1, except that the heated adhesive agent layer composition obtained in the step B is used instead of the adhesive agent layer composition obtained in the step A. Note that, in the second method, the adhesive agent layer composition is first heated to melt the drug and the like. Hence, the solvent and the like do not necessarily need to be introduced into the adhesive agent layer composition in the step A. In addition, in the second method, the heating is preferably conducted with stirring from the viewpoint of obtaining a more homogeneous adhesive agent layer composition in which the compounds contained are sufficiently melted. Moreover, the heating temperature and the heating time in the step B in the second method are the same as described above.

Moreover, when the patch of the present invention is produced by the second method, the laminating step mentioned in the first method may further be included after the step D2 and before the step C described later. On the other hand, when the above-described cutting step and packaging step are further conducted in the production of the patch of the present invention by the second method, these steps are preferably conducted after the step C described later.

The method for producing a patch of the present invention may be the first method or the second method. The first method is preferably employed from the viewpoint of ease of production. Moreover, the method for producing a patch of the present invention preferably further comprises the packaging step after the step D1 and before the step B, from the viewpoints of ease of production and stability of the pharmaceutical preparation.

<Step C>

The method for producing a patch of the present invention comprises a step C of cooling the heated adhesive agent layer composition to a temperature lower than the melting point of the drug at an average rate of temperature drop of 1 to 20° C./hour, thereby obtaining the adhesive agent layer comprising the drug at a supersaturated concentration in a dissolved form. The average rate of temperature drop refers to a rate found from the following formula: $(T_H - T_C)/\Delta t$, where $T_H$ is a temperature at the heating, $T_C$ is a temperature after the cooling, and $\Delta t$ is a time taken for the cooling. In addition, the temperature ($T_C$) after the cooling is not particularly limited, as long as the temperature is lower than the melting point of the drug. The temperature ($T_C$) is preferably 3 to 30° C., and more preferably 5 to 25° C., in general.

Such an average rate of temperature drop needs to be in a range from 1 to 20° C./hour. If the average rate of temperature drop is less than the lower limit value, further increase in the effect of suppressing the crystal precipitation of the drug cannot be expected by decreasing the average rate of temperature drop, and moreover such an average rate is not economically preferable. Meanwhile, if the average rate of temperature drop exceeds the upper limit value, the drug takes an amorphous form in the obtained adhesive agent layer, and the drug cannot be contained in a dissolved form. In addition, the average rate of temperature drop is preferably 2 to 18° C./hour, and more preferably 3 to 13° C./hour, from the viewpoint that there are tendencies that the drug can be more efficiently contained at a supersaturated concentration in a dissolved form in the adhesive agent layer, and that crystal precipitation of the drug can be suppressed for a longer period.

In the step C according to the present invention, the adhesive agent layer comprising the drug at a supersaturated concentration in a dissolved form can be obtained. In addition, the method for producing a patch of the present invention may further comprise the above-described laminating step, cutting step, and packaging step, and the like, if necessary.

The method for producing a patch of the present invention as described above makes it possible to obtain a patch of the present invention comprising the support layer, and the adhesive agent layer arranged on the at least one surface of the support layer, wherein the adhesive agent layer comprises at least one selected from the group consisting of the oxybutynin and the pharmaceutically acceptable salt thereof as the drug, at least one selected from the group consisting of the acrylic-based polymer and the rubber-based polymer as the adhesive base agent, the liquid paraffin, the organic acid, and the tackifier, and the drug is contained at a supersaturated concentration in a dissolved form.

In the patch of the present invention, preferred constitutions and contents of the oxybutynin and/or the pharmaceutically acceptable salt thereof, the acrylic-based polymer and/or the rubber-based polymer, the liquid paraffin, the organic acid, and the tackifier are the same as described above. In addition, unless the effects of the present invention are impaired, the adhesive agent layer according to the present invention may further comprise the drug other than oxybutynin, the adhesive base agent other than the acrylic-based polymer and the rubber-based polymer, the absorption enhancer, the plasticizer, the additive, and the like, which are mentioned in the description of the method for producing a patch of the present invention. The contents of these components are the same as described above.

In the patch of the present invention, the drug is contained at a supersaturated concentration in a dissolved form. Hence, excellent skin penetrability and excellent pharmaceutical physical properties such as adhesion and cohesiveness are achieved. Moreover, the patch of the present invention has an excellent long-term storability. Even in a long-term storage, crystals do not precipitate, and the skin penetrability and the pharmaceutical physical properties are retained at high levels.

Moreover, the method for producing a patch of the present invention can be adapted for a patch using a drug other than the oxybutynin and/or the pharmaceutically acceptable salt thereof. This makes it possible to obtain a patch in which the drug is contained at a supersaturated concentration in a dissolved form in the adhesive agent layer. Examples of such a drug include those listed above as the drugs other than oxybutynin.

Furthermore, the method for producing a patch of the present invention can be adopted for a patch using a plasticizer other than liquid paraffin. Examples of such a plasticizer include those listed above as the plasticizer.

EXAMPLES

Hereinafter, the present invention is described more specifically based on Examples and Comparative Examples. However, the present invention is not limited to Examples below at all. Note that DSC measurement and evaluation of crystal precipitation in each of Examples and Comparative Examples were carried out by the following methods.

<Differential Scanning Calorimetry (DSC Measurement)>

Figure 1B:
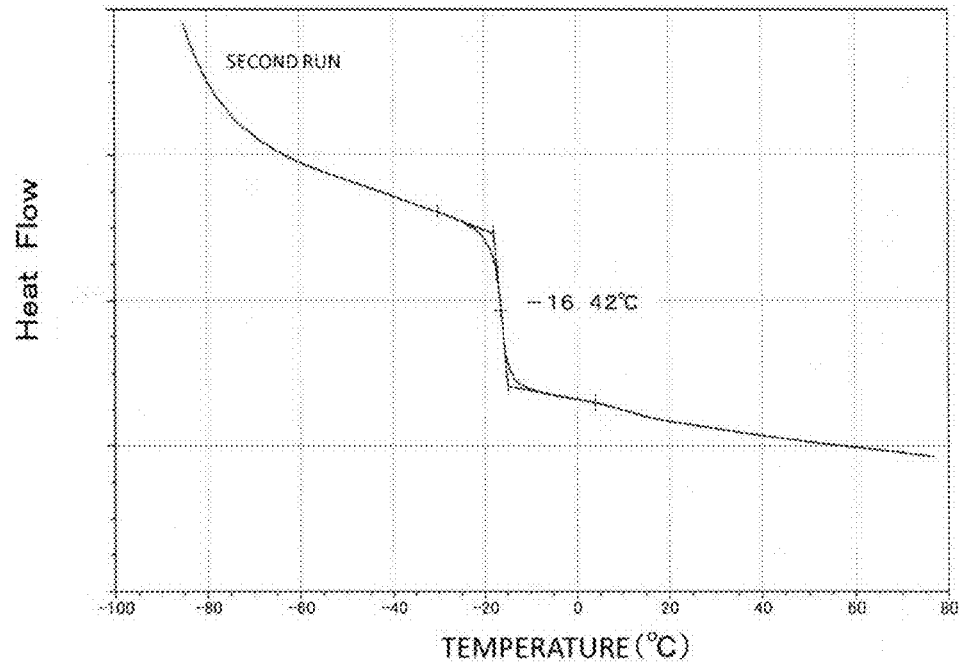
FIG. 1B is an enlarged graph in which the second run in the graph shown in FIG. 1A is enlarged in the longitudinal direction.

First, the melting point of crystals of the drug and the glass transition temperature of the drug in an amorphous form were determined. Specifically, DSC measurement was conducted in which crystals of oxybutynin was heated by using a differential scanning calorimeter ("Q-2000", manufactured by TA Instruments) from −90° C. to 80° C. at a rate of temperature rise of 10° C./min. From a peak observed in the obtained thermogram (first run), the endothermic melting point peak (melting point) was determined to be 59.44° C. Moreover, the sample subjected to the measurement for the endothermic melting point peak was cooled rapidly to −90° C. Then, DSC measurement was conducted by again raising the temperature from approximately −90° C. to approximately 80° C. From the baseline shift observed in the obtained thermogram (second run), the glass transition temperature in an amorphous form was determined to be −16.42° C. FIGS. 1A and 1B show graphs showing DSC measurement results of the crystals of oxybutynin.

Subsequently, the adhesive agent layer of each patch was subjected to DSC measurement by heating the adhesive agent layer from −90° C. to 80° C. at a rate of temperature rise of 10° C./min using the differential scanning calorimeter. Thus, the endothermic melting point peak at around 59.44° C. and the glass transition temperature at around −16.42° C. were observed. Note that a case where the melting point was observed indicates that the drug contained in the adhesive agent layer was in a crystal form.

A case where the glass transition temperature was observed indicates that the drug contained in the adhesive agent layer was in an amorphous form. A case where neither the melting point nor the glass transition temperature was observed indicates that the drug contained in the adhesive agent layer was in a dissolved form.

<Evaluation of Crystal Precipitation>

A surface of the adhesive agent layer of each patch was observed with naked eyes and a scanning microscope, and a state of crystal precipitation was evaluated based on the following criteria:

A: no crystals were detected with any of the naked eyes and the scanning microscope, B: crystals were detected with any of the naked eyes and the scanning microscope.

Example 1

First, 15 parts by mass of oxybutynin, 9 parts by mass of anhydrous sodium acetate, 2.5 parts by mass of anhydrous citric acid, 13.5 parts by mass of liquid paraffin, 2.3 parts by mass of 2-ethylhexyl acrylate-vinyl acetate copolymer, 20.7 parts by mass of styrene-isoprene-styrene block copolymer, 37.0 parts by mass of an alicyclic saturated hydrocarbon resin, and appropriate amounts of ethyl acetate and toluene were placed in a mortar, and sufficiently mixed with each other. Thus, 100 parts by mass (the entire mass of all the compounds excluding the solvents (toluene and ethyl acetate)) of an adhesive agent layer composition was prepared. Note that the concentration of oxybutynin contained in the adhesive agent layer composition (excluding the solvents (toluene and ethyl acetate)) was a supersaturated concentration.

Subsequently, the obtained composition was applied onto a release sheet made of polyethylene terephthalate, and the solvent was removed by drying. Then, a knitted fabric as a support layer made of a polyester was attached to a surface of the dried adhesive agent layer composition, the surface being opposite to the surface facing the release sheet. This article was tightly sealed in a packaging pouch made of a polyethylene/aluminum/polyacrylonitrile laminated film, and thus a packaged article was obtained. Subsequently, the packaged article, as it was, was heated to 60° C., and subjected to a heat treatment at the same temperature for 14 hours. Then, the packaged article was cooled to 25° C. over 3 hours (an average rate of temperature drop of 11.7° C./hour). Thus, a patch comprising a desired adhesive agent layer was obtained in the packaging pouch.

Immediately after the production, the patch was subjected to the evaluation of crystal precipitation. As a result, the evaluation was A, and no crystals were observed. In addition, DSC measurement was conducted on the adhesive agent layer of the patch immediately after the production, which was subjected to the evaluation of crystal precipitation. As a result, neither the endothermic melting point peak attributable to the crystals nor a baseline shift due to the glass transition attributable to the amorphous form was observed, indicating that the drug in the adhesive agent layer was in a dissolved form. Note that a baseline shift was observed at around −28° C. in the thermogram obtained by the DSC measurement. However, it was confirmed that the baseline shift was attributable not to the drug, but to the adhesive base agent, by comparing the thermogram with a thermogram obtained for a patch obtained in the same manner as in Example 1, except that no oxybutynin was used.

Comparative Example 1

A patch was obtained in a packaging container in the same manner as in Example 1, except that the heat treatment after the packaging was not conducted, and the dried adhesive agent layer composition, as it was, was used as the adhesive agent layer. Immediately after the production, the patch was subjected to the evaluation of crystal precipitation. As a result, the evaluation was A. However, a weak endothermic melting point peak attributable to crystals was observed in DSC measurement conducted on the patch, indicating that a trace amount of crystals of the drug were present in the adhesive agent layer.

Examples 2 to 5, Comparative Examples 2 to 8

Patches were obtained in the same manner as in Example 1, except that heat treatment conditions shown in Table 1 were employed, respectively.

Comparative Example 9

A patch was obtained in the same manner as in Example 1, except that the heat treatment conditions were 75° C. and 10 hours.

<Evaluation of Patches>

The patch in the packaging container obtained in each of Examples and Comparative Examples was allowed to stand at a temperature of 25° C. After being allowed to stand for 2, 4, 6, 12, 18, and 24 months, the patch was subjected to the evaluation of crystal precipitation and to the following skin penetrability test and evaluation of pharmaceutical physical properties.

(i) Skin Penetrability Test

First, dorsal skin was excised from a hairless mouse, and set to a flow-through cell where hot water of 37° C. was circulated through an outer peripheral portion thereof, with the dermis side being as a receptor side layer. Next, each of the patches obtained in Examples and Comparative Examples (preparation application area: 5 cm$^2$) was applied to the skin on the stratum corneum side. Saline was used as a receptor layer. The receptor solution was sampled at 5 ml/hr every 2 hours up to 24 hours. The flow volumes of the samples were measured, and the drug concentrations in the samples were measured by high performance liquid chromatography. From the obtained measurement values, the drug penetration rates per hour were calculated, and the drug penetration rate per unit area of the skin in a steady state was found. Note that a greater maximum value of the drug penetration rates (maximum skin penetration rate) obtained in 24 hours from the start of the test indicates a better skin penetrability.

(ii) Evaluation of Pharmaceutical Physical Properties

Each of the patches obtained in Examples and Comparative Examples was measured for adhesive force with a probe tack tester and a peel tester and for cohesive force (holding power) with a creep-testing machine, and the pharmaceutical physical properties were evaluated based on the following criteria:

A: both the adhesive force and the cohesive force were sufficient,

B: at least one of the adhesive force and the cohesive force was insufficient.

Figure 2:
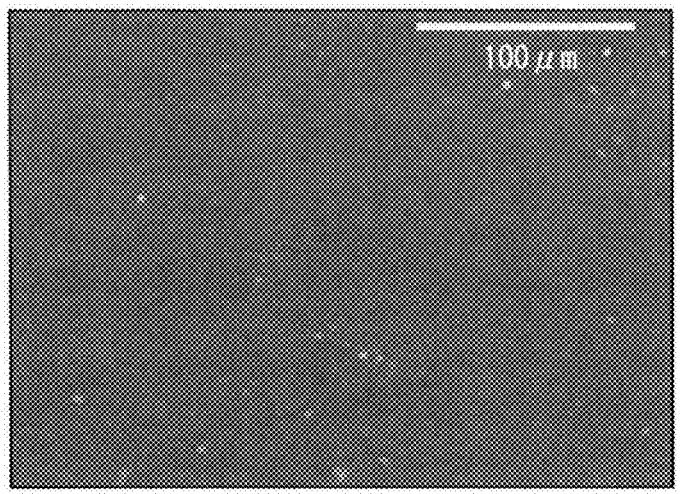
FIG. 2 is a scanning electron micrograph of a surface of an adhesive agent layer of a patch obtained in Example 1 and allowed to stand for 24 months.
Figure 3:
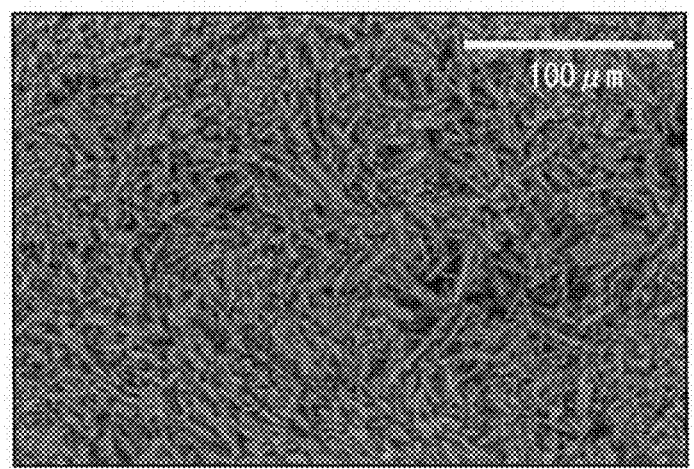
FIG. 3 is a scanning electron micrograph of a surface of an adhesive agent layer of a patch obtained in Comparative Example 1 and allowed to stand for 24 months.
Figure 4:
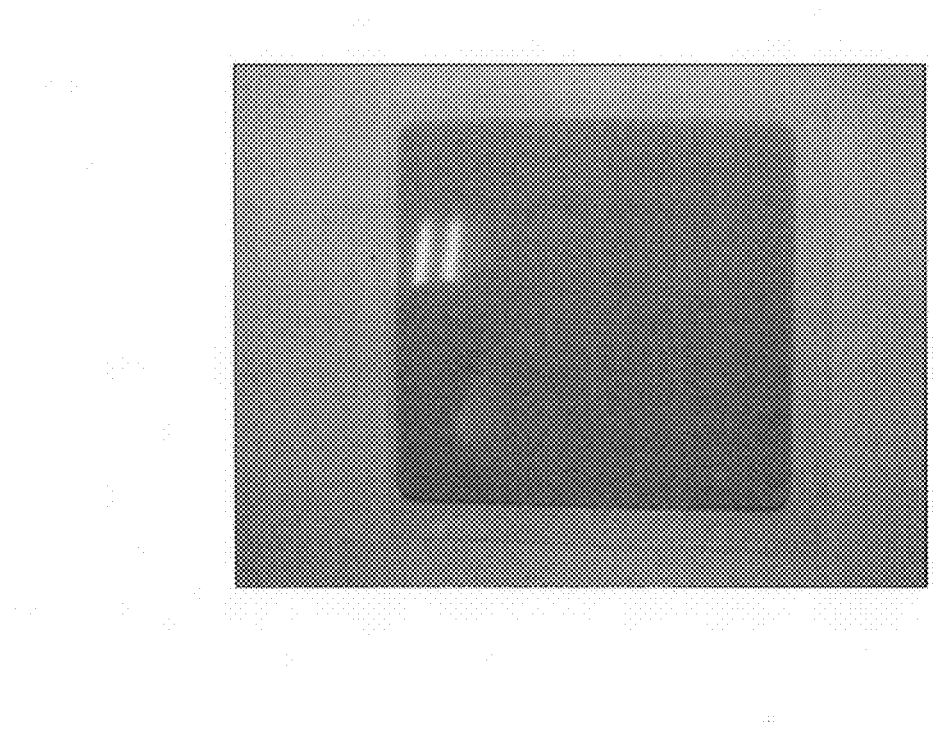
FIG. 4 is a photograph of the surface of the adhesive agent layer of the patch obtained in Example 1 and allowed to stand for 24 months.
Figure 5:
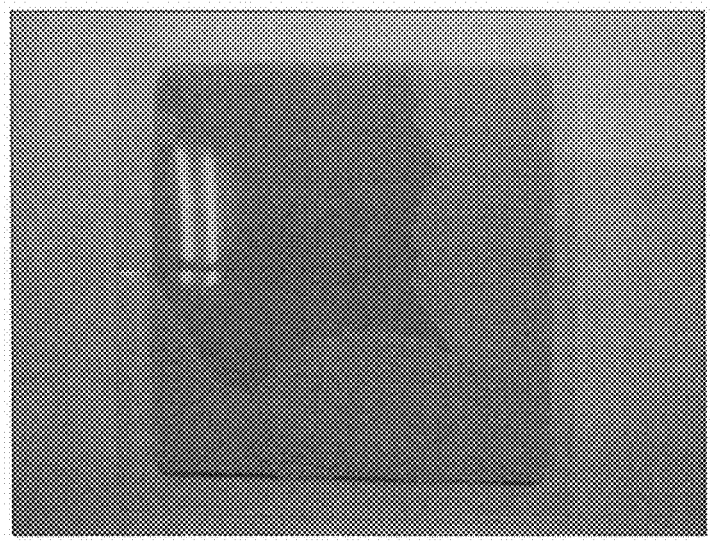
FIG. 5 is a photograph of the surface of the adhesive agent layer of the patch obtained in Comparative Example 1 and allowed to stand for 24 months.

Table 1 shows the results of the evaluation of crystal precipitation and the results of the pharmaceutical physical properties evaluation of Examples 1 to 5 and Comparative Examples 2 to 8, as well as the heating conditions in the production thereof. FIGS. 2 and 3 show scanning electron micrographs of surfaces of the adhesive agent layers of the patches obtained in Example 1 and Comparative Example 1 and allowed to stand for 24 months, respectively. FIGS. 4 and 5 show photographs of the surfaces of the adhesive agent layers of the patches obtained in Example 1 and Comparative Example 1 and allowed to stand for 24 months. In addition, the results of the skin penetrability test showed that the patches obtained in Examples 1 to 5 retained excellent skin penetrability, even after 24 months had elapsed. In contrast, the patches obtained in Comparative Examples 1 to 9 had insufficient skin penetrabilities. The skin penetrabilities were further lowered with the advance of the crystal precipitation, and the maximum skin penetration rates were lowered by 20% at the maximum, as compared with the patches obtained in Examples 1 to 5. Moreover, the patch obtained in Comparative Example 9 had insufficient pharmaceutical physical properties, and the evaluation result was B.

TABLE 1

| | Heating conditions | | Evaluation of crystal precipitation/ Evaluation of pharmaceutical physical properties | | | | | | |
|---|---|---|---|---|---|---|---|---|---|
| | Heating temperature (° C.) | Heating time (Hours) | Immediately after production | 2 months later | 4 months later | 6 months later | 12 months later | 18 months later | 24 months later |
| Example 1 | 60 | 14 | A/A | A/A | A/A | A/A | A/A | A/A | A/A |
| Example 2 | 60 | 8 | A/A | A/A | A/A | A/A | A/A | A/A | A/A |
| Example 3 | 60 | 24 | A/A | A/A | A/A | A/A | A/A | A/A | A/A |
| Example 4 | 64 | 14 | A/A | A/A | A/A | A/A | A/A | A/A | A/A |
| Example 5 | 69 | 14 | A/A | A/A | A/A | A/A | A/A | A/A | A/A |
| Comp. Ex. 1 | No heat treatment | | B/A | B/B | B/B | B/B | B/B | B/B | B/B |
| Comp. Ex. 2 | 60 | 0.5 | A/A | A/A | A/A | A/A | B/B | B/B | B/B |
| Comp. Ex. 3 | 60 | 1 | A/A | A/A | A/A | A/A | B/B | B/B | B/B |
| Comp. Ex. 4 | 50 | 1 | A/A | A/A | B/B | B/B | B/B | B/B | B/B |
| Comp. Ex. 5 | 50 | 8 | B/A | B/B | B/B | B/B | B/B | B/B | B/B |
| Comp. Ex. 6 | 50 | 24 | A/A | A/A | A/A | B/B | B/B | B/B | B/B |
| Comp. Ex. 7 | 40 | 24 | B/A | B/B | B/B | B/B | B/B | B/B | B/B |
| Comp. Ex. 8 | 40 | 72 | B/A | B/B | B/B | B/B | B/B | B/B | B/B |

As is apparent from the results of the DSC measurement and the results shown in Table 1, FIGS. 2 and 4, it was found that, in each of the patches obtained by the production method of the present invention, the drug was contained in a dissolved form in the adhesive agent layer from the immediate period after the production, and that the crystal precipitation was suppressed at a high level. Moreover, as is apparent from the results of the skin penetrability test and the evaluation of pharmaceutical physical properties, both a high level of skin penetrability and high levels of pharmaceutical physical properties were achieved in each of the patches of the present invention in which the drug was contained at a supersaturated concentration in a dissolved form in the adhesive agent layer.

Moreover, it was found that the skin penetrability and the pharmaceutical physical properties were retained even after long-term storage.

INDUSTRIAL APPLICABILITY

As described above, the present invention makes it possible to provide a method for producing a patch using oxybutynin and/or a pharmaceutically acceptable salt thereof as a drug, and also to provide a patch obtained by the method. Here, the method is capable of producing a patch which comprises the drug at a supersaturated concentration in a dissolved form in an adhesive agent layer, can be stored for a long period even under harsh conditions where no storage facility exists as in the case of the aftermath of the Great East Japan Earthquake, and can achieve both skin penetrability and pharmaceutical physical properties at high levels.

What is claimed is:

1. A method for producing a patch comprising a support layer and an adhesive agent layer arranged on at least one surface of the support layer, the method comprising:
    obtaining an adhesive agent layer composition comprising
        at least one drug which is free oxybutynin,
        an acrylic-based polymer and a rubber-based polymer as an adhesive base agent,
        liquid paraffin,
        an organic acid, and
        a tackifier;
    heating the adhesive agent layer composition at a temperature in a range from a melting point (° C.) of the drug to a temperature higher than the melting point by 10° C. for 8 to 24 hours; and
    cooling the heated adhesive agent layer composition to a temperature lower than the melting point of the drug at an average rate of temperature drop of 1 to 20° C./hour, thereby obtaining the adhesive agent layer comprising the drug at a supersaturated concentration in a dissolved form, wherein
    a content of the oxybutynin in the adhesive agent layer composition in terms of free oxybutynin is an amount which results in 10 to 50% by mass in the obtained adhesive agent layer,
    the adhesive agent layer composition comprises, as the adhesive base agent, the acrylic-based polymer and the rubber-based polymer at a mass ratio of 1:4 to 1:19, and
    a mass ratio of the oxybutynin to the liquid paraffin is 0.5:1 to 1.2:1 in the adhesive agent layer composition.

2. The method for producing a patch according to claim 1, wherein
    the content of the oxybutynin in the adhesive agent layer composition in terms of free oxybutynin is an amount which results in 10 to 20% by mass in the obtained adhesive agent layer.

3. The method for producing a patch according to claim 1, wherein
    the adhesive agent layer composition comprises, as the adhesive base agent, the acrylic-based polymer and the rubber-based polymer at a mass ratio of 1:5 to 1:10.

4. The method for producing a patch according to claim 1, wherein the mass ratio of the oxybutynin to the liquid paraffin is 0.7:1 to 1.2:1 in the adhesive agent layer composition.

5. The method for producing a patch according to claim 1, wherein
    the acrylic-based polymer is at least one selected from the group consisting of
        a) a copolymer of polymethyl methacrylate with a polyacrylate comprising at least one acrylate selected from the group consisting of 2-ethylhexyl acrylate, butyl acrylate, diacetone acrylamide, and tetraethylene glycol dimethacrylate,
        b) 2-ethylhexyl acrylate-N-vinyl-2-pyrrolidone-1,6-hexane glycol dimethacrylate copolymer,
        c) aminoalkyl methacrylate copolymer E, and
        d) 2-ethylhexyl acrylate-vinyl acetate copolymer.

6. The method for producing a patch according to claim 1, wherein
    the rubber-based polymer is at least one selected from the group consisting of styrene-isoprene-styrene block copolymer, styrene-butadiene-styrene block copolymer, styrene-butadiene rubber, polyisobutylene, isoprene rubber, and silicon rubber.

7. The method for producing a patch according to claim 1, wherein
    the organic acid is at least one selected from the group consisting of acetic acid, citric acid, and salts thereof.

8. The method for producing a patch according to claim 1, wherein
    the tackifier is at least one selected from the group consisting of hydrogenated rosin glycerin ester, alicyclic saturated hydrocarbon resins, aliphatic hydrocarbon resins, and terpene resins.

9. The method for producing a patch according to claim 1, further comprising, before heating,
    applying the adhesive agent layer composition onto the at least one surface of the support layer.

10. The method for producing a patch according to claim 1, further comprising, after heating and before the cooling,
    applying the heated adhesive agent layer composition obtained after heating onto the at least one surface of the support layer.

* * * * *